United States Patent [19]

Hilger

[11] Patent Number: Plant 6,350

[45] Date of Patent: Oct. 25, 1988

[54] HILGER'S CHERRY LAUREL

[76] Inventor: Robert R. Hilger, 11700 SW. 121 Ave., Dunnellon, Fla. 32630

[21] Appl. No.: 904,423

[22] Filed: Sep. 8, 1986

[51] Int. Cl.[4] ..... A01H 5/00

[52] U.S. Cl. ..... Plt./54

[58] Field of Search ..... Plt./51, 54

*Primary Examiner*—Robert E. Bagwill

*Attorney, Agent, or Firm*—Herbert W. Larson; Joseph C. Mason

[57] ABSTRACT

A new and distinct evergreen cherry laurel about 12 meters high at maturity. The leaves are oblong-lanceolate leathery in appearance and are distinguished by having a rich golden yellow color on green leaves 5 to 10 centimeters long at maturity.

1 Drawing Sheet

SUMMARY OF THE INVENTION

The present invention comprises a new and distinct variety of *Prunus caroliniana* called Hilger's Cherry Laurel; the variety being primarily characterized as a dense evergreen tree 12 m or more at maturity with oblong-lanceolate, leathery, yellow color in green leaves 5 to 10 cm long.

The variety has further non-distinguishing characteristics as follows:

Small, cream white flowers in racemes; and

Little shiny inedible black fruit.

This variety was originated by me by rooting of cuttings from a plant I found in a cultivated lot at 807 8th Ave. S.W. in Largo, Fla.

Subsequent to discovery of the new variety I successfully asexually reproduced it in my greenhouse located at Springdale Nursery, Inc., 11700 S.W. 121st Ave., Dunnellon, Fla. 32630 by rooting of cuttings. The reproductions have run true in all respects.

BRIEF DESCRIPTION OF THE PHOTOGRAPH

The color photograph illustrates the variety, including the distinguishing foliage and normal fruit.

DETAILED DESCRIPTION OF THE NEW VARIETY

Referring now specifically to the new and distinct variety of cherry laurel plant, the following is a detailed description. The specimen described was grown in Dunnellon, Fla.

Evergreen tree: 12 meters or more at maturity, vigorous, upright, dense, regular bearing of fruit after spring flowering.

Leaves: Oblong-lanceolate, leathery with distinctive variegated coloration on one or more leaves of chartruse, citron, mimosa and cream according to the Exotica, Volume 3, color chart. 5 to 10 cm long at maturity.

Flowers: Small, cream white in racemes.

Fruit: Small, shiny, inedible and black.

Use: Ornamental as a hedge.

In comparison to my new variety, *Prunus caroliniana* has glossy green leaves.

I claim:

1. A new and distinct plant of cherry laurel named Hilger's Cherry Laurel, as described and illustrated, and particularly characterized as to uniqueness by a distinct variegation of golden yellow in green, oblong-lanceolate, leathery leaves 5 to 10 cm longitudinally at maturity.

* * * * *

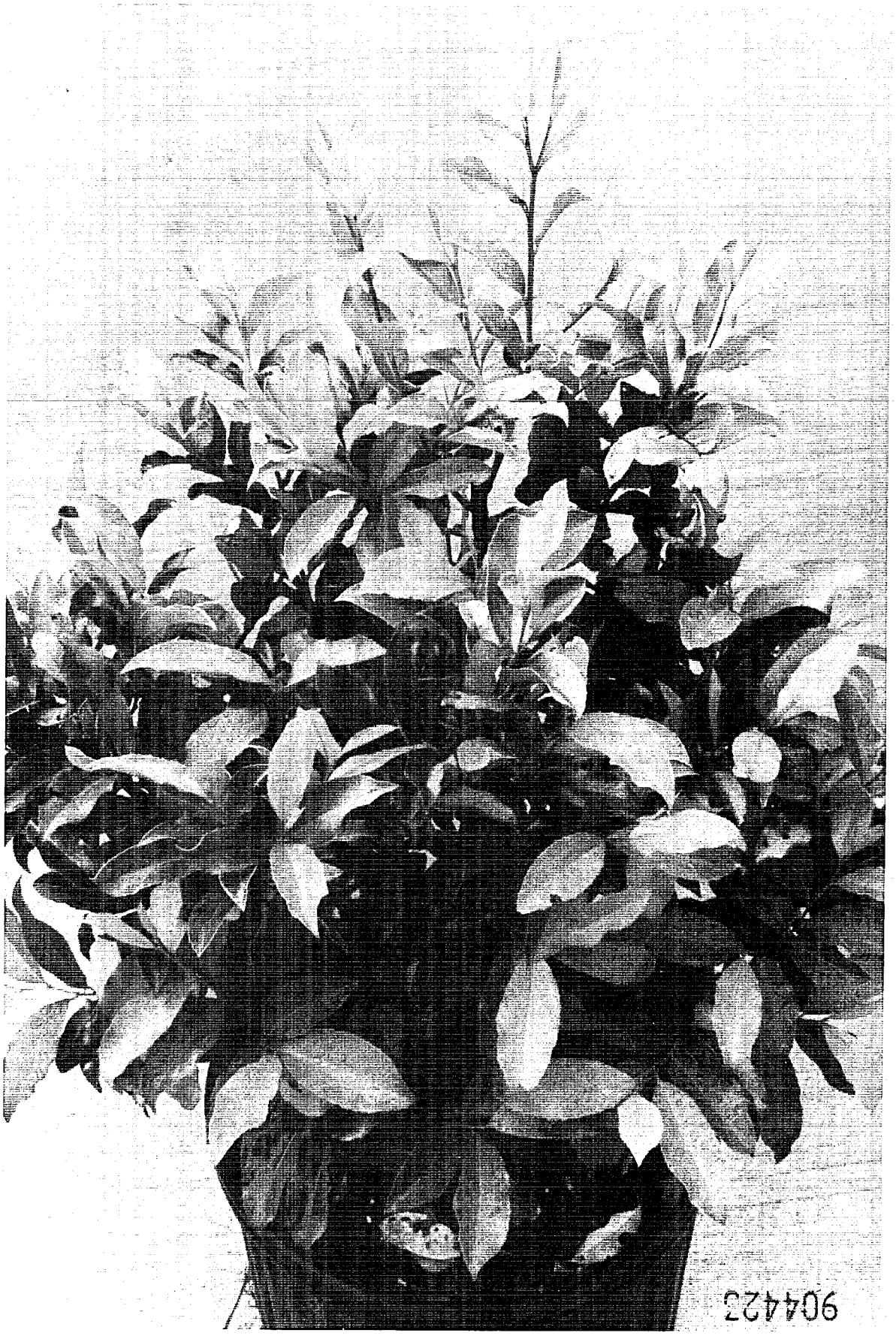
904423